United States Patent
Bacastow et al.

(10) Patent No.: US 7,488,323 B2
(45) Date of Patent: Feb. 10, 2009

(54) METHOD AND APPARATUS FOR MANIPULATING BONE DURING A SURGICAL PROCEDURE

(75) Inventors: David W Bacastow, Athens, GA (US); Kevin T Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 112 days.

(21) Appl. No.: 11/285,619

(22) Filed: Nov. 22, 2005

(65) Prior Publication Data

US 2006/0111729 A1 May 25, 2006

Related U.S. Application Data

(60) Provisional application No. 60/630,615, filed on Nov. 23, 2004.

(51) Int. Cl.
*A61F 5/00* (2006.01)
(52) U.S. Cl. ................................... 606/86 R
(58) Field of Classification Search .............. 606/86, 606/88, 89, 87, 104, 98, 96, 86 R
See application file for complete search history.

(56) References Cited

U.S. PATENT DOCUMENTS

| | | | | |
|---|---|---|---|---|
| 2,329,398 A | * | 9/1943 | Duffy | .......... 606/104 |
| 6,013,083 A | * | 1/2000 | Bennett | .......... 606/104 |
| 6,416,518 B1 | * | 7/2002 | DeMayo | .......... 606/96 |
| 6,802,844 B2 | | 10/2004 | Ferree | |
| 6,860,883 B2 | | 3/2005 | Janowski et al. | |
| 6,916,323 B2 | | 7/2005 | Kitchens | |
| 6,926,720 B2 | * | 8/2005 | Castaneda | .......... 606/98 |
| 6,929,647 B2 | | 8/2005 | Cohen | |
| 7,175,632 B2 | * | 2/2007 | Singhatat et al. | .......... 606/98 |
| 7,207,995 B1 | * | 4/2007 | Vandewalle | .......... 606/104 |
| 2004/0260298 A1 | * | 12/2004 | Kaiser et al. | .......... 606/72 |

OTHER PUBLICATIONS

Crowl, Adam C. et al., Closed Reduction and Percutaneous Fixation of Anterior Column Acetabular Fractures. Computer Aided Surgery, 7:169-178 (2002).

* cited by examiner

*Primary Examiner*—Pedro Philogene
(74) *Attorney, Agent, or Firm*—Harness, Dickey & Pierce, P.L.C.

(57) ABSTRACT

A method and apparatus for performing a procedure by manipulating a bone are disclosed. The apparatus can include a bone engaging portion and a digital manipulation portion. The bone engaging portion can engage the bone and then the digital manipulation portion can be used to manipulate the bone. The method can use the apparatus to perform a procedure with the apparatus.

9 Claims, 4 Drawing Sheets

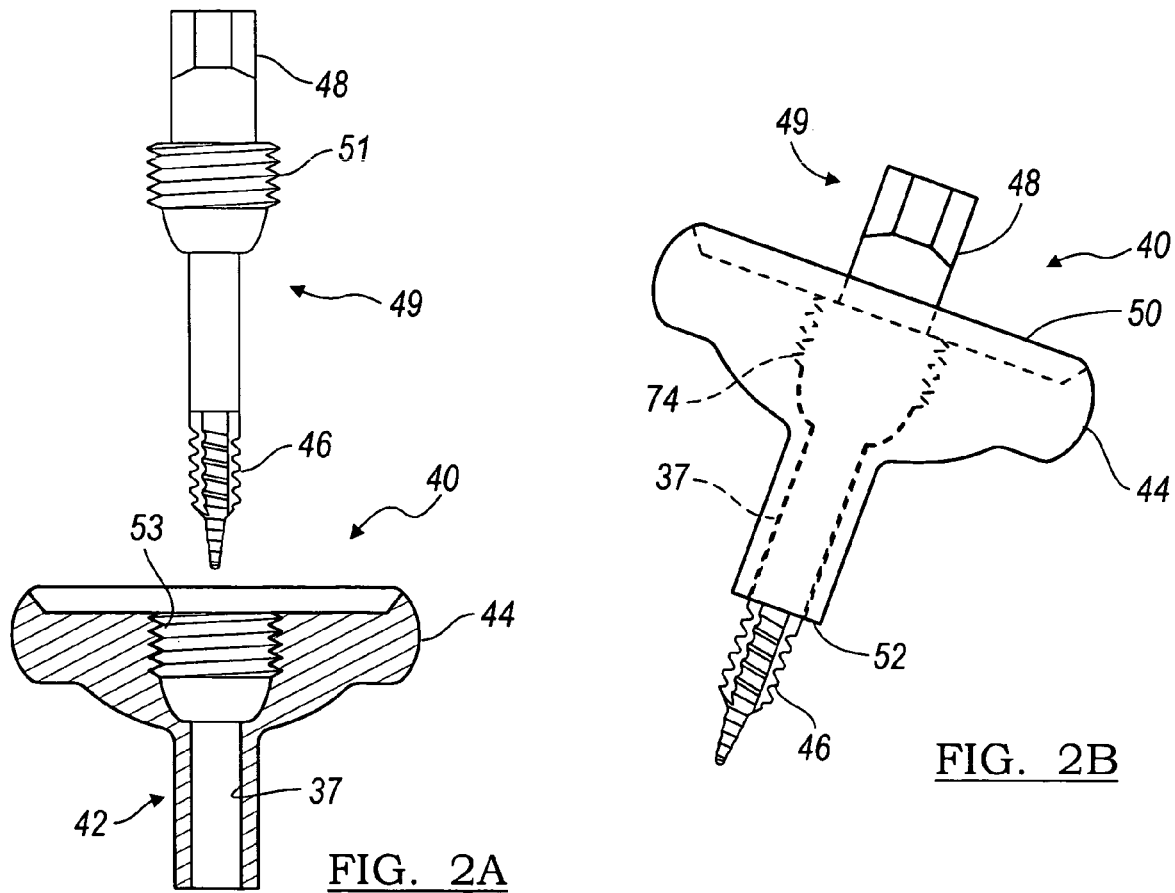
FIG. 2A
FIG. 2B
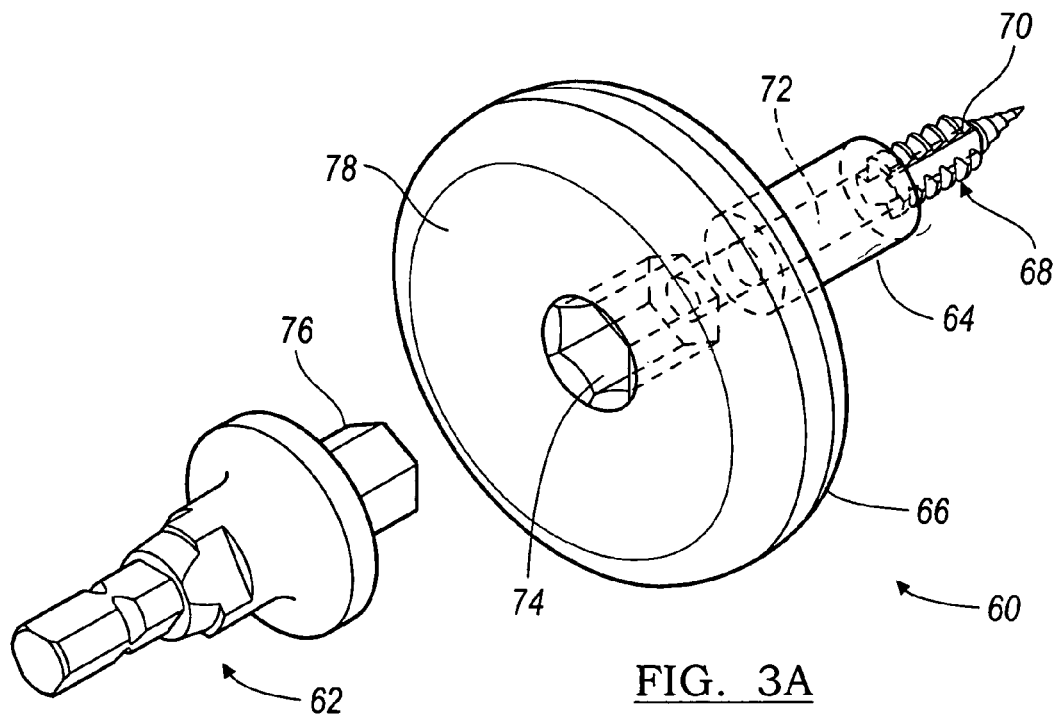
FIG. 3A

METHOD AND APPARATUS FOR MANIPULATING BONE DURING A SURGICAL PROCEDURE

CROSS-REFERENCE TO RELATED APPLICATIONS

This application claims the benefit of U.S. Provisional Application No. 60/630,615, filed on Nov. 23, 2004. The disclosure of the above application is incorporated herein by reference.

FIELD

A method and device for manipulating a bone during a procedure, in particular, a method and device for manipulating a selected bone for performing a surgical procedure.

BACKGROUND

Portions of the anatomy can generally be formed relative to one another to allow for a natural articulation, support, movement, or the like. Nevertheless, due to various circumstances, such as injury, disease, or the like, various portions of the anatomy can become damaged. For example, a bone portion may become damaged, including having a growth, or the like, in a manner that is substantially unnatural. It may be selected to perform a procedure relative to the bone portion to recreate the more natural bone portion.

For example, a resection of the distal clavicle using arthroscopy is a procedure that can be selected for treatment of arthritis that can affect the acrominoclavicualar joint. In the resection procedure, a portion of the end of the clavicle affected by the arthritic condition can be removed. The removal of the portion of the clavicle can be performed with a burr that can be inserted subacromial from below the clavicle and viewed with an arthroscope. It will be understood that any appropriate procedure can be performed, such as resection with a burr, a saw, removal of bone spur, or the like. Nevertheless, it can be selected to apply pressure to the dorsum of the clavicle to manipulate and position it. Commonly, it is attempted to move the clavicle with no attachments or tools.

Generally, it is attempted to maneuver the clavicle with hand pressure to the dorsum of the clavicle to bring it into view of the arthroscope for viewing by a user, such as a physician. It can be difficult to position the clavicle in a selected position due to lack of understanding of anatomy by an assistant, swelling or tissue volume in the surgical area, other damage to the anatomy in the surgical area, or the like.

Therefore, it is desired to provide a method and apparatus to move a bone into a selected area for performing a surgical procedure on the selected bone or relative to the selected bone. It will be understood that the bone that can be manipulated can be any appropriate bone, such as the clavicle. It may be desirable to provide a method and apparatus to move the bone without vast experience of the specific anatomy or the surgical procedure. Although, it will be understood that it is also desirable to provide a method and apparatus for a user, such as a surgeon, to both position the bone and perform a procedure relative to the bone.

SUMMARY

The method and apparatus taught herein can assist in achieving a selected quality and consistency of an arthroscopic resection of the distal clavicle. An apparatus can include a device that can interconnect with the clavicle, or any appropriate bone, and include various ergonomical portions that allow for orientating, moving, locating, and the like of the clavicle bone. The device can allow for ease of attachment and detachment from the bone, such as the clavicle, during and after a procedure. Generally, an incision can be made relative to the dorsum of the distal clavicle through which the device can be inserted and operably attached to the clavicle. A portion of the device, such as an ergonomically compatible head portion, can remain exterior of a patient's body, such as above the skin of the patient. The device can allow a surface for applying the pressure to manipulate the clavicle to the proper position and orientation within the operative field, where the surgeon may perform the required resection.

According to various embodiments, a manipulation device for interconnection with a bone of an anatomy is disclosed. The device can include a body member and a digital manipulation portion extending from a first end of the body. A bone attachment mechanism can extend from a second end of the body. The digital manipulation portion is operable to move the bone when the bone attachment mechanism is engaged in the bone.

According to various embodiments, a manipulation device to be interconnected with a bone portion in an anatomy is disclosed. The device can include a main body portion extending a distance from a first end to a second end and a head portion extending from the first end of the body for manipulation by a user. The device can also include a threaded member extending from the second end of the body to threadably engage the bone and a stabilization portion extending from the second end to engage the bone.

According to various embodiments a method of manipulating a bone portion in an anatomy with a manipulation device interconnected with the bone portion is disclosed. The method can include providing a bone manipulation device having a bone engaging portion and a digital manipulation portion. The bone engaging portion can engage the bone and a force can be applied to a clavicle to dislocate it from the acromioclavicular joint. Also, a procedure can be performed on the anatomy.

Further areas of applicability of the present teachings will become apparent from the detailed description provided hereinafter. It should be understood that the detailed description and various examples, while indicating the various embodiments, are intended for purposes of illustration only and are not intended to limit the scope of the teachings.

BRIEF DESCRIPTION OF THE DRAWINGS

The present teachings will become more fully understood from the detailed description and the accompanying drawings, wherein:

FIG. 2A is an exploded partial cross-sectional view of a bone manipulation device according to various embodiments;

FIG. 2B is a perspective view of a bone manipulation device according to various embodiments;

FIG. 3A is a top perspective exploded view of a bone manipulation device according to various embodiments;

DETAILED DESCRIPTION OF VARIOUS EMBODIMENTS

The following description of the various embodiments is merely exemplary in nature and is in no way intended to limit the teachings, their application, or uses.

Figure 1A:
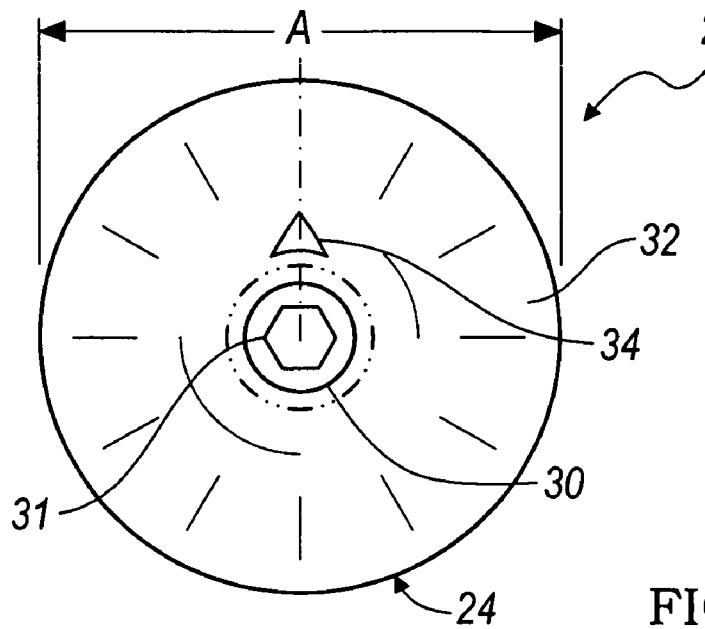
FIG. 1A is a top view of a bone manipulation device according to various embodiments.
Figure 1B:
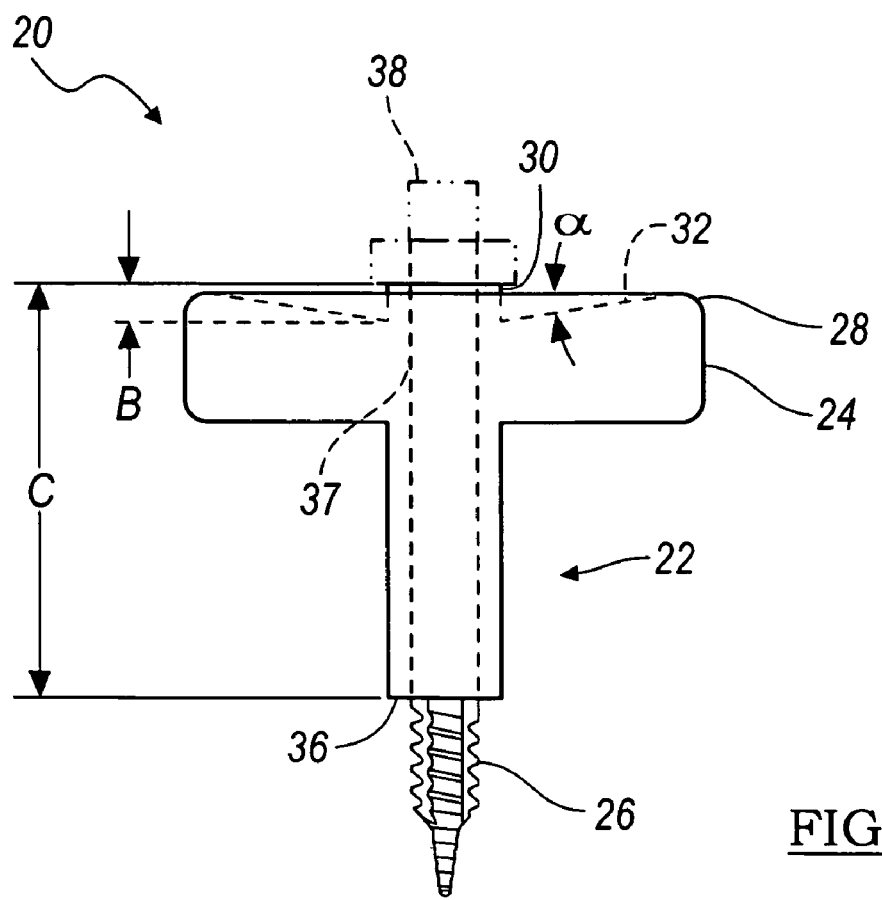
FIG. 1B is a side plan view of the device of FIG. 1A.

With reference to FIGS. 1A and 1B, a bone manipulation device 20 is illustrated. The bone manipulation device 20 can include various portions such as a body or extending member 22, a head portion or first manipulation portion 24, and a attachment mechanism 26. The attachment mechanism 26 can extend from an end of the body 22 that is generally opposite of the end from which the head portion 24 extends. The various portions can be formed in any appropriate manner, such as a generally ergonomic manner for use by a user, such as a physician. For example, the head portion 24 may be substantially annular or round in shape or it can be any other appropriate geometrical shape or configuration. Further, the head portion 24 can include an upper rounded edge 28 for contact by a user or portion of a user such as a finger. Further the body can be formed in any appropriate shape or configuration, such as a cylinder, a polygon, or the like. Also, a manipulation stem or member 30 can extend from the head portion 24 for contact by a selected portion.

Any appropriate portion of the device 20 can define a driver portion 31. For example, an internal hex drive 31 can be defined within the manipulation member 30. It will be understood, however, that the drive portion 31 can be defined by any appropriate portion of the device 20. For example an external drive can be defined on the manipulation member 30 or any appropriate portion of the device 20.

The bone manipulation device can be formed of any appropriate material such as a metal, metal alloy, polymer, or the like. It will be further understood that various portions of the bone manipulation device 20 can be formed from a plurality of materials. For example, the attachment mechanism 26 can be formed of a first metal alloy while the body 22 is formed of a second metal alloy.

The bone manipulation device 20 can be provided in a plurality of configurations or shapes, as briefly mentioned above. For example, the size, shape, and configuration of the bone manipulation device 20 can be provided to allow and encourage thumb pressure to be applied through the bone manipulation device 20 to a selected bone, such as the clavicle. It will be understood that the bone manipulation device 20, or a bone manipulation device according to various embodiments, can be used to apply a force or manipulate a bone in any appropriate manner. Applying a force to the clavicle is merely exemplary of various embodiments.

The head portion 24 can include any appropriate dimension, such as a diameter A. The diameter A can be any appropriate diameter, such as about 30 mm. Nevertheless, the diameter A can be any appropriate dimension such as about 1 mm to about 50 mm. The head portion 24 and the manipulation stem 30 can be provided for digital manipulation, such as manipulation by a finger of a user, of the bone manipulation device 20.

The head portion 24, as discussed above, can include any appropriate configuration or geometry. For example, a top 32 of the head portion 24 can define a concavity having an angle α. The angle α can be any appropriate angle, such as about 12°. It will be understood, however, that the angle α can be any appropriate angle such as about 5° to about 25°. The concavity defined in the top portion through a head portion 24, can be provided for various reasons such as allowing for ergonomic and ease of use of the bone manipulation device 20, such as containing a portion of a finger of a user. The top 32 can also define a convex surface or a substantially flat surface. Thus, it will be understood, that a concavity or any other shape is not required.

The manipulation stem 30 can extend from the top portion 32 in any appropriate dimension. For example, the stem 30 can extend a distance B above the top 32 of the head portion 24. The distance B can be any appropriate dimension, such as about 7 mm. Nevertheless, the manipulation stem 30 can be provided in any appropriate dimension such as about 1 mm to about 20 mm. The manipulation stem 30 can be provided for various purposes and in various geometries for various purposes. For example, the manipulation stem 30 can provide a point or area for applying a force with the bone manipulation device 20 such as in directing pressure with the bone manipulation device 20.

Further, the device 20 can include a direction or orientation indicator 34. The indicator 34 can be any appropriate indication, such as an arrowhead, a triangle, or the like. Further, the indicator 34 can be formed to contrast with the material of the device 20, such as a bright color, a luminescent material, or the like. The indicator 34 can indicate a direction relative to the bone into which it is positioned, a patient into which it is positioned, or any appropriate indication.

The body 22 can be formed in any appropriate dimension. The body 22 can be any appropriate geometry that does not include a cylinder, such as a polygon, a square, or the like. The body 22, however, can include a dimension, such as a diameter, that can provide stability after positioning of the bone manipulation device 20, ease of orientation of the bone manipulation device 20, or any appropriate purpose. For example, the attachment mechanism 26 can engage a selected portion of the anatomy, such as a bone. An edge or ledge 36 can be defined by the body 22 and can engage a portion of the anatomy, such as a surface of the bone, to provide stability of the bone manipulation device 20 relative to the bone.

The bone manipulation device 20 can generally include a dimension C, such as a height. The dimension C can be any appropriate dimension such as about 25 mm. The dimension C of the bone manipulation device 20 can include a dimension that is designed and selected for various situations, patients, and the like. For example, the dimension C can account for the amount of soft tissue surrounding a selected bone portion, a swelling relative to an area of operation, or the like. Further, the dimension C can be selected pre-operatively, intra-operatively, or at any appropriate time. For example, it will be understood that the body 22 can be substantially modular from the head 24. Therefore, the body 22 can be selected from a plurality of sizes to interconnect with the selected head 24 before positioning of the bone manipulation device 20 relative to a patient.

The attachment mechanism 26 can be any appropriate attachment mechanism. For example, the attachment mechanism 26 can be a threaded portion that is formed as a single member with the body 22 and head 24, formed as a separate member and attached to the body 22 or passed through a bore 37 defined by the bone manipulation device 20. As discussed above, the threads can be self-tapping, drilling, or the like. The attachment mechanism 26 can be provided to be interconnect with, engage with, or as a single member with the bone manipulation device 20. Regardless of the interaction the bone manipulation device 20 can be positioned relative to an anatomy as a single unit. The attachment mechanism 26, according to various embodiments, can also be any appropriate size. For example, the attachment mechanism can have a diameter that is about 4 mm to about 5 mm.

The bore 37, however, can be defined by the bone manipulation device 20 and can receive or allow for passage of an anchor or screw 38, illustrated in phantom, for fixing or holding the bone manipulation device 20 relative to a selected bone or portion of the anatomy. Therefore, it will be understood that the bone manipulation device 20 can be provided as a single member, an integral assembly, or a plurality of members that are assembled at an appropriate time, such as during an operative procedure. The separate screw 38 can be provided in any appropriate manner and can be any appropriate screw. Further, the attachment mechanism 26 can be provided in any appropriate manner, such as including threads, a pin, a staple, self-tapping threads, self-driving threads, or any appropriate attachment mechanism.

With reference to FIGS. 2A and 2B, a bone manipulation device 40, according to various embodiments is illustrated. The bone manipulation device 40 can include a portion similar to the bone manipulation device 20. For example, the bone manipulation device 40 can include a body portion 42 from which a head portion 44 can extend from a first end and an attachment mechanism 46 can extend from a second end. Further, a drive stem 48 can extend from the head portion 44. Each of the portions, including the body 42, the head 44, the attachment mechanism 46, and the stem 48, can be formed of a similar or different materials. For example, metals, metal alloys, polymers, or other selected materials can be used to form the various portions of the bone manipulation device 40.

The attachment mechanism 46 and the driver stem 48 can be integrally formed or formed from a single member in an attachment driver assembly 49. The assembly 49 can include a connection portion 51 that engages a connection portion 53 of the head portion 44. The connection portions 51, 53 can include complimentary threads such that the driver assembly 41 can be interconnected with the head portion 44 in a selected manner. Further, the body portion 42 can define a bore or throughbore, such as the throughbore 37 so that the attachment assembly 49 can pass through the head portion 44 and the body portion 42. The interconnection portion 51, 53, can then allow for the driver attachment assembly 49 to apply a force to the attachment mechanism 46 to allow for the device 40 to rest upon a selected bone, as discussed above.

It will be understood that the manipulation device 40 can be inserted into a selected bone in any appropriate manner, such as first interconnecting the driver attachment assembly 49 with the head portion 44 and driving the assembly into the bone. The driver stem 48 can be formed from material or connected to the assembly so that it will break away from the driver attachment assembly 49 under a selected load or torque. Therefore, the driver stem 48 can provide a torque limiting feature to the bone manipulation device 40. It will also be understood, however, that the driver stem 48 can be later used for distal manipulation of the bone manipulation device 40 if it is selected to allow the driver stem 48 to not break away under a selected load.

It will be understood that the various portions of the bone manipulation device 40 can be formed of various materials. For example, the driver attachment assembly 49 can be formed of a plurality of materials. The attachment mechanism 46 can be formed of a metal or metal alloy that is interconnected with the driver portion of the driver attachment assembly 49. Further the head portion 44 and the body portion 42 can be formed of a material that is either similar to or different from either of the materials for the driver portion 48 or the attachment mechanism 46. It will be understood that the materials may be selected for any appropriate purposes, such as force transfer, torque limitation, or the like.

Although it will be understood that the various portions can be provided separately for use by a user, it can be provided as an integrally formed unit. Further, the bone manipulation device 40, according to various embodiments, can be formed of a plurality of portions or be formed of a single member during a formation process.

The attachment mechanism 46 can be formed integrally with the body 42, the head 44, and even the stem 48 if selected, or formed as a separate member, including those discussed above and herein. Therefore, the attachment mechanism 46 can be passed through the body 42, formed as a single member with the body 42, integrally attached to the body 42 (e.g. with an adhesive or welding), or the like. Also, the attachment mechanism 46 can define threads that are self-tapping and/or self-drilling and can also be any other appropriate attachment mechanism.

It will be understood that the various dimensions of the bone manipulation device 40 can be similar to the dimensions of the bone manipulation device 20 according to various embodiments. Further, the head portion 44 can include an upper surface 50 that is concave similar to the concavity of the upper surface 32 of the bone manipulation device 20. The top 50, however, can also be formed convexly or substantially flat, according to various embodiments.

The body portion 42 can define a ledge 52 that can rest upon or engage a surface of a bone to provide for a stable base of the bone manipulation device 40 once it is positioned relative to a bone. It will be understood that the ledge 52 can be any appropriate dimension. The body 42 can also include any appropriate cross-sectional configuration to provide for a selected positioning or engagement between the bone manipulation device 40 and the bone upon which it is positioned or which it is positioned near.

Figure 3B:
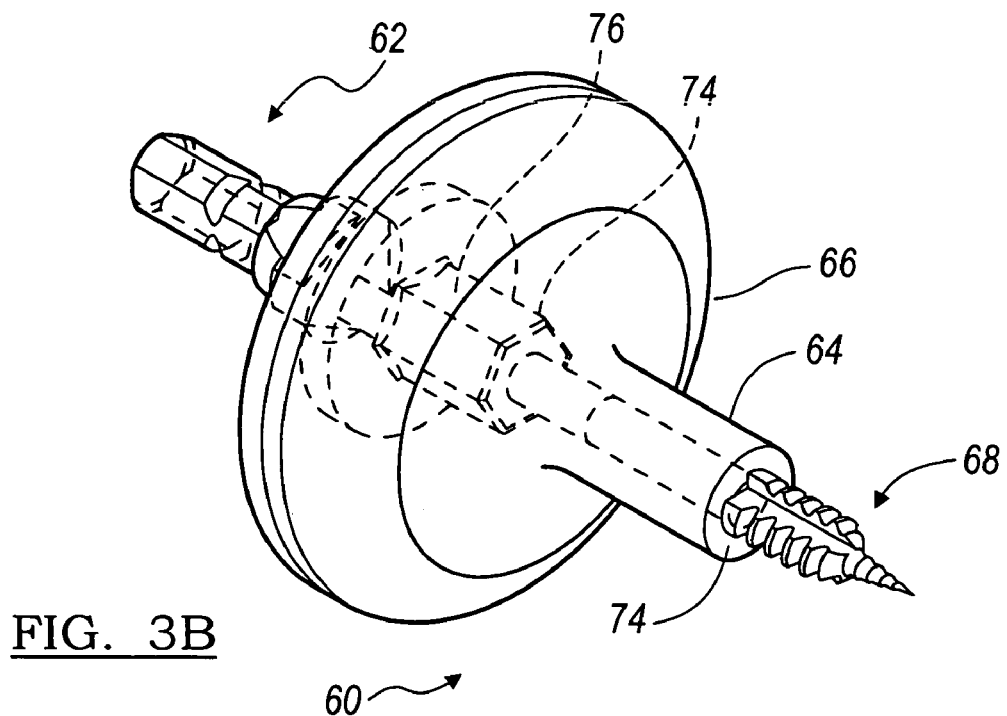
FIG. 3B is a bottom assembled perspective view of the device of FIG. 3A.

With reference to FIGS. 3A and 3B, a bone manipulation device 60, according to various embodiments, is illustrated. The bone manipulation device 60 can be driven with a driving member or mechanism 62 or any appropriate driving mechanism. The bone manipulation device 60 can be interconnected with the driving member 62 for driving the bone manipulation device 60 into a selected bone, manipulating the bone, or any combination thereof. Therefore, the driving member 62 can also act as a manipulation stem, as discussed above, or it can only be used to drive the bone manipulation device 60 into a selected bone.

The bone manipulation device 60 can define a body 64 and a head portion 66. As discussed above, the body 64 and the head portion 66 can be assembled together, formed as a single member, or modular for various purposes. Further, an attachment mechanism 68 can also be provided to interconnect the bone manipulation device 60 with a selected bone. The attachment mechanism 68 can be any appropriate attachment mechanism and can include a threaded member that has passed through a bore defined by the bone manipulation device 60, formed as a single member with the body 64, or integrally interconnected with the body 64.

For example, as illustrated here, the attachment mechanism 68 can include a threaded portion 70 that extends exteriorly from the body 64. Extending into the body 64 can be a shaft portion 72 that forms an interference fit with the body member 64. The shaft member 72 can be adhered into the body 64, welded to the body 64, or positioned therein in any appropriate manner. Further, the distal end of the body 64 can define a ledge 74, as discussed above, for engaging a selected bone to provide a stability of the bone manipulation device 60 during use of the bone manipulation device 60.

The head portion 66 can define a driving bore that can be formed in any appropriate manner such as complementary to a driving portion 76 of the driving member 62. The driving portion 76 can engage the driving bore 74 for driving the bone manipulation device 60 into a selected bone. For example, the driving bore 74 can define a hexagonal recess while the driving portion 76 defines a hexagonal outer surface. Therefore, an interference fit can be formed between the driving portion 76 and the driving bore 74 to allow for driving the bone manipulation device 60 into the selected bone portion.

The driving member 62 can be used with any appropriate driving mechanism such as a hand-powered drill, a pneumatic drill, an electrical drill, or any appropriate portion. Further, the driving member 62 can include a torque limiting mechanism that can allow for limiting amount of torque that can be provided through the attachment mechanism 68 to the bone. This can reduce or eliminate possible stripping of the bone into which the bone manipulation device 60 is positioned or other possible side effects of positioning the bone manipulation device 60 into a bone.

Further, the driving bore 74 can be used to receive a manipulation stem, such as that discussed above. A manipulation stem, not here illustrated, can be interconnected with the bone manipulation device 60 at any appropriate time for manipulating a selected bone portion.

Also, the head portion 66 can define the top surface 78 that can include a concavity similar to the concavity of the top portion 32 of the bone manipulation device 20. The top surface 78 of the head portion 66 can also be formed in any appropriate configuration such as flat, convex, or the like.

It will be understood that the various portions of the bone manipulation device 60 and the driving member 62 can be formed of any appropriate materials. For example, metals, metal alloys, polymers, and the like can be used to form any of the portions of the bone manipulation device 60. Further, the bone manipulation device 60 and the driving member 62 can be formed of a plurality of materials intermixed for selected purposes. For example, a polymer can be used to interconnect the attachment mechanism 68 with the body 64.

The bone manipulation device 60 can include any appropriate dimensions, such as dimensions similar to the bone manipulation device 20. Nevertheless, it will be understood that the dimensions of the bone manipulation device 60, or bone manipulation device according to any of the various embodiments, can be provided to achieve a selected result. Further, the various portions of the bone manipulation device, such as the head 66 and the body 64 can be substantially modular and interconnected for a selected procedure.

Figure 4:
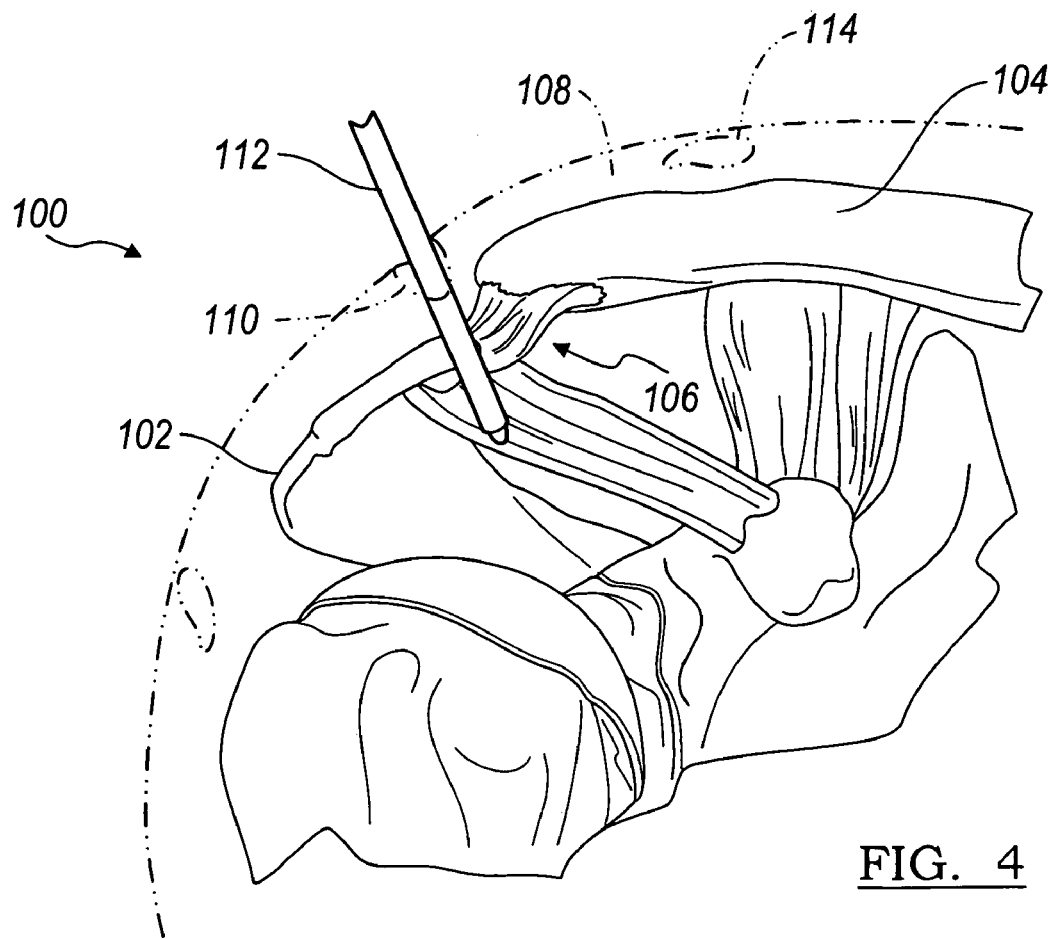
FIG. 4 is a detailed view of an anatomical view of the acrominoclavicualar joint, including representative soft tissue around the joint.
Figure 5:
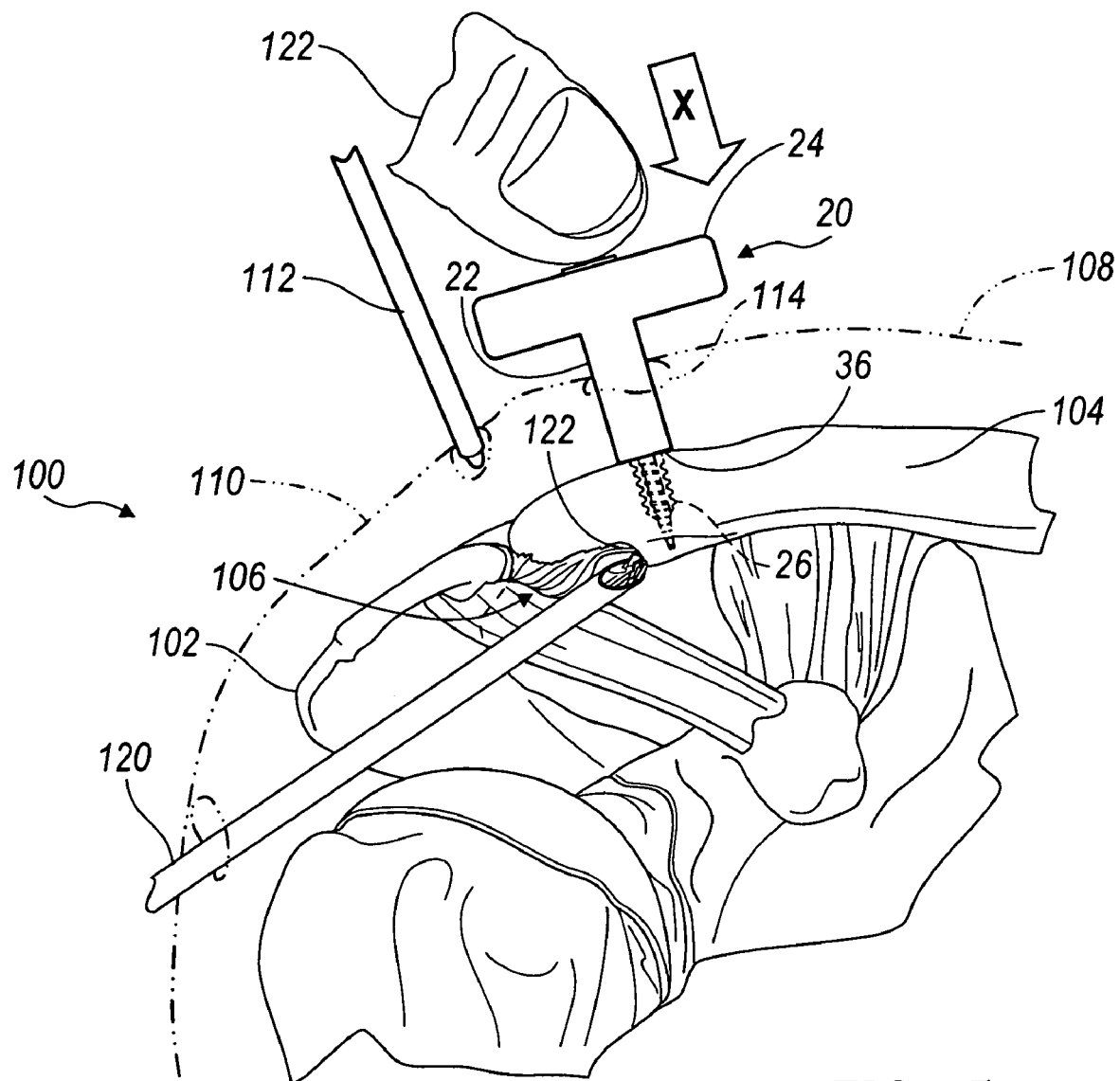
FIG. 5 is an environmental view illustrating a bone manipulation device interconnected with the clavicle according to various embodiments.

With reference to FIGS. 4-5, a method of using a bone manipulation device according to various embodiments as illustrated. Although the bone manipulation device 20 is illustrated in performing a procedure relative to a clavicle 104, it will be understood that the bone manipulation device, according to various embodiments, can be used to perform a plurality of procedures. For example, a plurality of bones can be aligned relative to one another, can be moved relative to one another, a plurality of bone segments can be aligned relative to one another, or moved relative to one another, for any appropriate procedure. Therefore, although the method is exemplary described in relation to the bone manipulation device 20 and a procedure relative to the clavicle 104, a procedure can be performed relative to any appropriate bone portion.

With initial reference to FIG. 4, an anatomy of a patient 100 can include acromion process 102 and the clavicle 104 that can include an articulating portion, such as the acromioclavicular joint 106. The various bony portions can be covered by soft tissue 108, including skin and the like. The soft tissue 108 can have portals formed therein to obtain access to the various bony portions, such as the clavicle 104. For example, a first incision 110 can be formed to allow for access of an arthroscope 112. The arthroscope 112 can be used to view various portions of the anatomy, such as the clavicle 104. A second portal 114 can also be formed through the soft tissue 108 to allow access to the clavicle 104 or any portion of the anatomy for various purposes.

The second portal 114 can be provided to allow positioning of the bone manipulation device 20 relative to the clavicle 104. The second portal 114 can be formed in any appropriate manner such as with an incision, a stab wound, or the like. Regardless, the second portal 114 through the soft tissue 108 can allow access for the bone manipulation device 20 to be interconnected with the clavicle 104.

With additional reference to FIG. 5, the bone manipulation device 20 can be inserted and/or interconnected with the clavicle 104. The portal 114 can be made into soft tissue in any appropriate manner such as after identifying the clavicle 104 with a digital exam. The incision 114 can be made over the dorsum of the distal clavicle approximately 2.5 centimeters medial of the acromioclavicular joint 106. It will be understood that any appropriate identification process such as an x-ray, a scan, or the like, can be used to determine the position of the clavicle 104. Further, the incision, as discussed above, can be formed in any appropriate manner and in any appropriate size. For example, the incision 114 may be selectively sized to be substantially no greater than or equivalent to the diameter of the body portion 22. Therefore, the incision 114 can be defined as a small or minor incision.

The clavicle 104 can be prepared for interconnection with the bone manipulation device 20 through any appropriate procedure. For example, a pilot hole or a preparation bore can be formed in the clavicle 104 to allow for an engagement of the attachment mechanism 26. The bone manipulation device 20 can then be positioned relative to the clavicle 104 in any appropriate manner.

For example, the arthroscope 112 can be used to view the clavicle 104 and the attachment mechanism 26 of the bone manipulation device 20. Therefore, the bone manipulation device 20, including the attachment mechanism 26 can be easily inserted in the pilot hole formed in the clavicle 104. Nevertheless, a substantially blind insertion can also be used where the bone manipulation device 20 is walked along the clavicle until it engages the pilot hole and then the bone manipulation device 20 can be inserted into the clavicle 104.

Further, it will be understood, that the bone manipulation device can include the attachment mechanism 26 that is appropriately designed to not require a pilot hole. Regardless, the attachment mechanism 26 can be threaded into the bone 104 and can include self-tapping or self-drilling threads, such as that discussed above. Regardless, the ledge 36, or any appropriate portion of the bone manipulation device 20, can engage the clavicle 104 at a selected time to limit drilling of the attachment mechanism 26 into the bone 104. Further, as discussed above, the ledge 36 can be provided to allow for a stable base of the bone manipulation device 20 relative to the clavicle 104.

Various procedures can be performed relative to the clavicle 104 using the arthroscope 112 for viewing of the clavicle 104 or the acromioclavicular joint 106. Regardless, a tool, such as a burr 120, can be used to perform a procedure relative to the clavicle 104, such as performing a resection thereof. A resected portion 122 of the clavicle 104 can be formed with the tool 120 in any appropriate manner. Nevertheless, to obtain access to the clavicle 104, or to move the portion of the clavicle 104 that is to be resected into view of the arthroscope 112 it may be selected to move the clavicle 104 in a selected manner. Therefore, the bone manipulation device 20 can be used to move the clavicle 104 generally in the direction of the arrow X such that the resected portion 122, or the portion of the clavicle 104 to be resected, is in better view of the arthroscope 112. A user, such as a surgeon 122, can engage the bone manipulation device 20 to move in the direction of arrow X. Alternatively, or in addition thereto, an assistant can efficiently manipulate the bone manipulation device 20 to assist in moving the clavicle 104 in a selected manner for ease of preparation for performing a procedure relative to the clavicle 104 by a surgeon.

It will be understood, however, that the bone manipulation device 20, or the bone manipulation device according to any of the various embodiments, can be used to manipulate, move, orient any appropriate bone portion for a selected procedure. Although it is illustrated that the clavicle 104 can be moved relative to the acromion 102, any appropriate bone can be moved relative to any appropriate bone portion with the bone manipulation device. For example, a humerus can be moved relative to the glenoid, the femur can be moved relative to the acetabulum, or any appropriate manipulation portion.

The teachings are merely exemplary in nature and, thus, variations that do not depart from the gist thereof are intended to be within the scope of the teachings. Such variations are not to be regarded as a departure from the spirit and scope of the teachings.

What is claimed is:

1. A method of manipulating a clavicle to dislocate it from the acromioclavicular joint in an anatomy with a manipulation device interconnected with the bone portion, the method comprising:
    providing a bone manipulation device having a bone engaging portion and a digital manipulation portion;
    engaging the bone engaging portion with the clavicle bone;
    applying a force to the clavicle bone through the bone manipulation device to dislocate the clavicle bone from the acromioclavicular joint; and
    performing a procedure on the anatomy.

2. The method of claim 1, further comprising:
    forming a first portal in a soft tissue surrounding the bone.

3. The method of claim 2, wherein engaging the bone engaging portion into the bone includes:
    passing the bone engaging portion through the formed first portal;
    threading the bone engaging portion into the bone; and
    stabilizing the bone manipulation device relative to the bone.

4. The method of claim 1, wherein performing a procedure on an anatomy includes resecting a portion of the clavicle bone while applying the force to the bone manipulation device to move the clavicle bone to a selected position.

5. The method of claim 1, further comprising:
    observing with an arthroscope a procedure being performed on the anatomy.

6. The method of claim 1, further comprising:
    interconnecting the bone engaging portion with the bone; and
    maintaining the digital manipulation portion of the bone manipulation device exterior to a soft tissue portion of the anatomy;
    wherein applying a force to the bone manipulation device includes applying a force to the digital manipulation portion while the bone engaging portion engages the bone.

7. The method of claim 1, further comprising:
    wherein performing a procedure includes aligning various segments of a single bone.

8. The method of claim 1, further comprising:
    limiting a force applied to the bone manipulation device with a torque limiting drive mechanism.

9. The method of claim 1, further comprising:
    attaching a manipulation stem with a driving bore formed in a head portion of the bone manipulation device;
    wherein engaging the bone engaging portion includes positioning a driver in the driving bore and applying a force to the bone engaging portion to move the bone engaging portion into the bone.

* * * * *

UNITED STATES PATENT AND TRADEMARK OFFICE
CERTIFICATE OF CORRECTION

PATENT NO. : 7,488,323 B2
APPLICATION NO. : 11/285619
DATED : November 22, 2005
INVENTOR(S) : David W. Bacastow et al.

It is certified that error appears in the above-identified patent and that said Letters Patent is hereby corrected as shown below:

In column 1, line 32; *"acrominoclavicualar"* should read --*acromioclavicular*--

In column 2, line 66; *"acrominoclavicualar"* should read --*acromioclavicular*--

In column 3, line 14; *"a" should be* --*an*--

In column 4, line 62; *delete "be"* (second occurrence)

In column 5, line 27; *delete "a"*

Signed and Sealed this

Thirtieth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.        : 7,488,323 B2
APPLICATION NO.   : 11/285619
DATED             : February 10, 2009
INVENTOR(S)       : David W. Bacastow et al.

Page 1 of 1

It is certified that error appears in the above-identified patent and that said Letters Patent is hereby corrected as shown below:

In column 1, line 32; *"acrominoclavicualar"* should read --*acromioclavicular*--

In column 2, line 66; *"acrominoclavicualar"* should read --*acromioclavicular*--

In column 3, line 14; *"a"* should be --*an*--

In column 4, line 62; *delete "be"* (second occurrence)

In column 5, line 27; *delete "a"*

This certificate supersedes the Certificate of Correction issued June 30, 2009.

Signed and Sealed this

Twenty-eighth Day of July, 2009

JOHN DOLL
*Acting Director of the United States Patent and Trademark Office*